United States Patent [19]

Katayama

[11] Patent Number: 5,461,073
[45] Date of Patent: Oct. 24, 1995

[54] SEPTICEMIA SUPPRESSING SUBSTITUTION FLUID PREPARATION

[75] Inventor: Masami Katayama, Tokyo, Japan

[73] Assignee: Kanegafuchi Kagaku Kogyo Kabushiki Kaisha, Osaka, Japan

[21] Appl. No.: 293,889

[22] Filed: Aug. 22, 1994

[30] Foreign Application Priority Data

Aug. 24, 1993 [JP] Japan .................................. 5-232529

[51] Int. Cl.[6] .................................................. A61K 31/19
[52] U.S. Cl. ............................................................. 514/557
[58] Field of Search ............................................. 514/557

[56] References Cited

U.S. PATENT DOCUMENTS 5,292,774  3/1984  Hiraide et al. ........................ 514/557

FOREIGN PATENT DOCUMENTS 0355453  2/1990  European Pat. Off. .

OTHER PUBLICATIONS

Maximal Activities of Glutaminase and Some Enzymes of Glycolsis and Ketone Body Utilization and Rates of Utilization of Glutamine, Glucose and Ketone Bodies by Intestinal Mucosa After Burn Injury–M.S.M. Ardawi et al, Burns (1987) vol. 16, No. 6, pp. 438–444.

Inhibition of TPN–Associated Intestinal Mucosal Atrophy With Monoacetoacetin Scott A. Kripke, M.D. et al, Journal of Surgical Research (1988), vol. 44, No. 4, pp. 436–444.

Effect of DL–3–Hydroxybutyrate Infusions on Leucine and Glucose Kinetics in Burned Rats Receiving TPN–Alberto Maiz et al, The Journal of Nutrition, (1986) vol. 116, No.1.

*Primary Examiner*—Kimberly R. Jordan
*Attorney, Agent, or Firm*—Armstrong, Westerman, Hattori, McLeland & Naughton

[57] ABSTRACT

A septicemia suppressing substitution fluid preparation for controlling bacterial translocation of intestinal bacteria into blood containing at least one compound selected from the group consisting of (R)-3-hydroxybutyric acid and salts thereof is provided. In condition of septicemia, bacterial translocation of intestinal bacteria into blood is suppressed.

6 Claims, No Drawings

SEPTICEMIA SUPPRESSING SUBSTITUTION FLUID PREPARATION

BACKGROUND OF THE INVENTION

1. Field of the Invention

The present invention relates to a substitution fluid preparation for suppressing bacterial translocation (hereinafter referred to as BT) of intestinal bacteria into blood and, more particularly, to a substitution fluid preparation containing (R)-3-hydroxybutyric acid and/or its salts for suppressing BT in case of BT-induced septicemia caused by injury to intestinal mucosa of a patient.

2. Description of the Prior Art

As to applications for 3-hydroxybutyric acid, it is described in Japanese Laid-open Patent Publication No. 201746/'83 that a pharmaceutical composition containing (R)-3-hydroxybutyric acid, salts derived from this acid or salts of amino acids is effective for metabolism of and protection against cardiac muscle.

It is also described in Japanese Laid-open Patent Publication No. 502942/'86 that dialytic fluid better suited for the condition of patients than any conventional dialytic fluid is obtainable by adding a mixture of (R)3-hydroxybutyric acid salts and acetoacetic acid salts as ketone bodies to the dialytic fluid instead of sodium acetate.

It is also known that the ketone bodies ((R)-3-hydroxybutyric acid and acetoacetic acid) are excellent energy sources for peripheral blood vessel tissue and importance as energy sources for (R)-3-hydroxybutyric acid consists in suppression of protein catabolism and improvement of metabolic acidosis.

Further, as to a substitution fluid preparation comprising (R)-3-hydroxybutyric acid and its salts, in Japanese Laid-open Patent Publication No. 191212/'90 there is described an application example of 3-hydroxybutyric acid as a supplementing extracellular fluid and a maintaining substitution fluid and actual examples given, in which it was applied to patients in acute stage. Although, while in these examples it is emphasized that it is an excellent energy source for patients in actual stage, no description is made for other applications.

For patients with their vitality decreased due to grave disorders or diseases, a great problem for life-saving is that infection and septicemia are inevitable in the course of treatment. With, for example, grave post-operation patients, patients of autoimmunity, patients with tumor, traumatized patients, burned patients etc, it is often the case that decrease of vitality gives rise to septicemia to result in death. As to this problem, study has been made by many researchers. For example, Deitch E. A. et al. reported cases in which BT resulted through intestinal canal membrane (J. Trauma, 1985 25, 385–392). Nothing, however, has been written about an effective means for controlling this BT.

SUMMARY OF THE INVENTION

An object of the present invention is to provide a septicemia suppressing substitution fluid preparation containing at least one compound selected from the group consisting of (R)-3-hydroxybutyric acid, (RS)-3-hydroxybutyric acid and salts thereof.

Another object of the present invention is to provide a method for suppressing septicemia of a patient in a state of energy-deficiency in the gut-tract by administering a substitution fluid preparation containing at least one compound selected from the group consisting of (R)-3-hydroxybutyric acid, (RS)-3-hydroxybutyric acid and salts thereof.

Other objects and advantages of the present invention will become apparent to those skilled in the art from the following detailed description.

The present inventor gave attention to this BT and found out, from the results of an experiment he made with burned rats, that the BT is apparently controllable by a substitution fluid containing 3-hydroxybutyric acid, its salts and its amino acid additives.

DETAILED DESCRIPTION OF THE INVENTION

The present invention provides, in a first aspect, a septicemia suppressing substitution fluid preparation for controlling bacterial translocation of intestinal bacteria into blood containing at least one compound selected from the group consisting essentially of (R)-3-hydroxybutyric acid, (RS)-3-hydroxybutyric acid and pharmaceutically acceptable salts thereof.

The present invention provides, in a second aspect, a method for suppressing septicemia of a patient in a state of energy-deficiency in the gut-tract, which comprises administering to said patient a substitution fluid preparation consisting essentially of an effective amount of at least one compound selected from the group consisting essentially of (R)-3-hydroxybutyric acid, (RS)-3-hydroxybutyric acid, a pharmaceutically acceptable salt thereof, and a pharmaceutically acceptable carrier to suppress bacterial translocation from the gut-tract to the blood of said patient.

(R)-3-hydroxybutyric acid is same as (D)-3-hydroxybutyric acid in configuration and is useful as (R)-isomer (D-isomer) alone or in combination with (S)-isomer (L-isomer) as, for example, racemic body.

As pharmaceutically acceptable salts of (R)-3-hydroxybutyric acid, there are included, among others, alkali metal salts such as sodium and potassium, alkaline earth metal salts such as calcium and magnesium, and organic base-derived salts involving amino acid salts, hence they are all usable if they are salts conventionally used medically as ingredients of substitution fluid preparations or recognized as usable as such. As amino acids, preferred are natural amino acids, especially neutral amino acids or basic amino acids. Proper concentration of the salts may somewhat vary depending on the kinds of salts but it is preferred to be in a range of 0.3–3% by weight.

Besides the effective ingredients of (R)-3-hydroxybutyric acid and/or its salts, as pharmaceutically acceptable carriers, mainly for supplying energy, glucose, sucrose, maltose, fructose, dextran, D-sorbitol, mannitol, xylitol etc. may be used singly or in combination of two or more. For supplying nutrients, essential amino acids, lipids and inorganic salts etc. may be added. Proper concentration thereof may be in a range used for ordinary substitution fluid preparations.

Substitution fluid preparations of the present invention are preferred to be in a pH range of 4–9, more preferably in a range of 4–8, and still more preferably in a range of 5–8, as in the case of conventional ones. As to osmotic pressure (ratio), it is preferred to be adjusted to approximately 1.0.

The patients the substitution fluid preparations of the present invention are applicable to, are those suffering from septicemia who are in a state of energy-deficiency in the gut-tract and in a state of their BT not controllable due to a failure of the so-called gastrointestinal (or gut) mucousal barrier function. Generally, it is often the case that the substitution fluid preparations of the present invention are applied to grave post-operation patients and patients in acute stage showing septicemic condition or likely to have such possibility.

Hereinafter, examples of the compositions of the substitution fluid preparations of the present invention will be given.

Substitution fluid A:

| | | |
|---|---|---|
| (R)-3-sodium hydroxybutyrate (m mol/L) | 79 | (content: approx. 1%) |
| Sodium lactate (m mol/L) | 18.2 | |
| Glucose (m mol/L) | 505.1 | |
| Sodium chloride (m mol/L) | 30.4 | |
| Potassium chloride (m mol/L) | 18.2 | |
| Magnesium chloride (m mol/L) | 1.35 | |
| pH: 7.5 | | |

Substitution fluid B:

| | |
|---|---|
| (R)-3-sodium hydroxybutyrate (m mol/L) | 59 |
| (R)-3-potassium hydroxybutyrate (m mol/L) | 20 |
| Sodium lactate (m mol/L) | 18.2 |
| Glucose (m mol/L) | 505.1 |
| Sodium chloride (m mol/L) | 65.6 |
| Magnesium chloride (m mol/L) | 1.35 |
| pH: 7.5 | |

Substitution fluid C:

| | |
|---|---|
| (R)-3-hydroxybutyrate acid (m mol/L) | 79 |
| (S)-lysine (m mol/L) | 70 |
| Glucose (m mol/L) | 448 |
| Sodium chloride (m mol/L) | 30.4 |
| Potassium chloride (m mol/L) | 18.2 |
| Magnesium chloride (m mol/L) | 1.35 |
| pH: 7.0 | |

Substitution fluid D:

| | |
|---|---|
| (R)-3-sodium hydroxybutyrate (m mol/L) | 70 |
| (R)-3-potassium hydroxybutyrate (m mol/L) | 18 |
| (R)-3-magnesium hydroxybutyrate (m mol/L) | 1.5 |
| Sodium lactate (m mol/L) | 18.2 |
| Glucose (m mol/L) | 486 |
| Sodium chloride (m mol/L) | 50. |
| pH: 7.6 | |

Hereinafter, the present invention will be described in greater detail by way of examples but the present invention is by no means limited thereby.

As test solutions A and C, the aforementioned substitution fluids A and C were used, respectively.

The test method and the composition of the comparative test solution used in the examples were as described below.

[Test methods]

Test method 1:

Burned rats were prepared in the following way. Each back of healthy rats was shaven approximately. 20% and a burn of about degree 3 was prepared by the method of Walker et al. (Walker HL, J. Trauma, 1968, 8, 1049–1051) with simultaneous insertion of a catheter into the central vein.

Then 20 ml/kg/hr of Ringer's solution with addition of lactic acid was administered for resuscitation. Thereafter, it was shifted to the the test solution and administration was made for 64 hours at a rate of 10 ml/kg/hr.

Test method 2:

The rats used in the test were grown rats 190–220 g in weight and 32 thereof were divided into 4 groups, of which 2 groups were burned on the back by the test method 1 to prepare rats with burns. With the other 2 groups of rats, approximately 20% of the back was shaven and subjected to the same operation as in the test method 1 (normal rats).

Test method 3:

72 hours after thermal injury, laparotomy was made with the rats after taking blood samples from artery, parts of intestinal canal membrane lymph node, liver, spleen and cecum were excised respectively as specimens.

Test method 4:

The specimens were homogenated and 0.2 ml thereof was uniformly sprayed over MacConky's medium and a sheep blood medium and cultivation was made for 24 hours at 37° C. With MacConky's medium, the number of gram-negative bacteria and with the sheep blood medium, the number of colonies of all bacteria were determined. With intestinal canal membrane lymph node, the number of colonies per rat's weight (CFU/g) was determined, while with liver and spleen, the number of colonies per gram of organs was calculated respectively.

Test method 5:

With the blood samples taken, biochemical examination was made for judgment of blood function and mobility.

[Substitution fluid as comparative test solution]

| | |
|---|---|
| Sodium lactate (m mol/L) | 97.2 |
| Glucose (m mol/L) | 505.1 |
| Sodium chloride (m mol/L) | 30.4 |
| Potassium chloride (m mol/L) | 18.2 |
| Magnesium chloride (m mol/L) | 1.35 |
| pH: 7.5 | |

Example 1

According to the aforementioned test methods 1–5, the test solution A and the comparative test solution were administered to both burned rats and normal rats and the results shown in Table 1 and Table 2 were obtained by analysis of rats' blood samples taken 72 hours after injury.

TABLE 1

Concentrations of gas partial pressure, hematocrit and sodium in artery

| | Burned rats | | Normal rats | |
|---|---|---|---|---|
| | Test solution A | Comp. test solution | Test solution A | Comp. test solution |
| pH | 7.50 ± 0.02 | 7.51 ± 0.02 | 7.46 ± 0.02 | 7.49 ± 0.02 |
| $O_2$ partial pressure (torr) | 85 ± 3 | 86 ± 3 | 84 ± 5 | 83 ± 5 |
| $CO_2$ partial pressure (torr) | 45 ± 3 | 46 ± 2 | 44 ± 3 | 46 ± 2 |
| Surplus base (m mol/L) | 8.6 ± 0.4 | 8.9 ± 1.1 | 7.3 ± 0.7 | 8.0 ± 0.9 |
| hematocrit (%) | 37.4 ± 2.5 | 37.9 ± 1.7 | 41.4 ± 2.3 | 41.8 ± 1.1 |
| Sodium (m mol/L) | 133 ± 1 | 135 ± 1 | 136 ± 1 | 134 ± 2 |

TABLE 2

Concentrations of ketone bodies, glucose, fatty acids and transferrin in artery

| | Burned rats | | Normal rats | |
|---|---|---|---|---|
| | Test solution A | Comp. test solution | Test solution A | Comp. test solution |
| Acetoacetic acid ($\mu$mol/L) | 47 ± 7 | 42 ± 5 | 64 ± 9 | 78 ± 9 |
| 3-hydroxy-butyric acid ($\mu$mol/L) | 241 ± 32 | 128 ± 17 | 284 ± 18 | 279 ± 33 |
| Total ketone bodies ($\mu$mol/L) | 288 ± 34 | 171 ± 17 | 348 ± 20 | 357 ± 39 |
| Glucose (m mol/L) | 7.1 ± 0.4 | 7.0 ± 0.4 | 7.0 ± 0.5 | 7.5 ± 0.3 |
| NEFA (m Eg/L) | 0.26 ± 0.02 | 0.28 ± 0.04 | 0.39 ± 0.04 | 0.37 ± 0.04 |
| Transferrin | 0.41 ± 0.01 | 0.41 ± 0.01 | 0.42 ± 0.01 | 0.41 ± 0.01 |

From the results shown in Table 1 and Table 2, the following points can be confirmed:

(1) Alkalolysis was not noted with both groups of burned rats and normal rats.

(2) $O_2$ partial pressure and $CO_2$ partial pressure of blood were normal with both groups without any difference therebetween.

(3) Regarding 3-hydroxybutyric acid concentration of the ketone bodies in blood, the comparative test solution administered group of burned rates was abnormally low.

The 3-hydroxybutyric acid concentration of blood of the test solution A-administered group of burned rats was, however, close to that of the group of normal rats, which indicates its active absorption and metabolism as an energy ingredient.

The conclusion based on the results of the blood analysis was that administration of a substitution fluid containing (R)-3-hydroxybutyric acid to burned rats indicated that its absorption and metabolism was proceeding normally as an energy ingredient, this attesting its bio-suitability as a substitution fluid.

Example 2

After administration of each of the test solutions to both groups of burned rats and normal rats individually, treatment was carried out according to the test methods 3 and 4. The results were as shown in Table 3.

TABLE 3

Internal organs BT of rats

| | Burned rats | | Normal rats | |
|---|---|---|---|---|
| | Test solution A | Comp. test solution | Test solution A | Comp. test solution |
| Intestinal canal membrane lymph node BT occurrence rate (%) | 100 | 100 | 87.5 | 100 |
| BT colony forming units (CFUs/g) | 217 ± 62 | 724 ± 256 | 182 ± 50 | 213 ± 56 |
| Liver Bt occurrence rate (%) | 12.5 | 62.5 | 0 | 0 |
| Spleen BT occurrence rate (%) | 12.5 | 62.5 | 0 | 0 |
| Total aerobic bacteria in intestines (log 10 CFUs/g) | 10.1 ± 0.2 | 10.4 ± 0.2 | 9.5 ± 0.2 | 9.6 ± 0.1 |
| Gram-negative bacteria in intestines (log 10 CFUs/g) | 10.1 ± 0.2 | 10.4 ± 0.2 | 8.7 ± 0.2 | 8.8 ± 0.1 |

From the results shown in Table 3, the following points are noted as effects of the test solution A on burned rats:

(1) The number BT colony forming units in intestinal canal membrane lymph node was significantly less than in cases where the comparative test solution was used.

(2) BT occurrence rates for liver and spleen were significantly less.

These test results indicate that administration of (R)-3-hydroxybutyric acid has a BT controlling effect.

Example 3

The test solution C was administered to 2 burned rats and, as in Example 2, its BT controlling effect on each organ was examined. The results were as shown in Table 4.

TABLE 4

|  | Burned rats Test solution C |
|---|---|
| Intestinal canal membrane lymph node BT occurrence rate (%) | 100 |
| BT colony forming units (CFUs/g) | 215 ± 60 |
| Liver BT occurrence rate (%) | 0* |
| Spleen BT occurrence rate (%) | 0* |

*No BT occurrence was observed for the two burned rats.

As mentioned above, the present invention provides a BT-controlling substitution fluid preparation which is effective when it is administered to a patient suffering or possibly suffering from septicemia due to lowering or loss of BT controlling effect, which is attributable to its gastrointestinal barrier function failure.

What is claimed is:

1. A method for suppressing septicemia of a patient in a state of energy-deficiency in the gut-tract, which comprises administering to said patient a substitution fluid preparation consisting essentially of an effective amount of at least one compound selected from the group consisting of (R)-3-hydroxybutyric acid, (RS)-3-hydroxybutyric acid and a pharmaceutically acceptable salt thereof, together with a pharmaceutically acceptable carrier to suppress bacterial translocation from the gut-tract to the blood of said patient.

2. The method according to claim 1, wherein said pharmaceutically acceptable salt is an alkali metal salt, an alkaline earth metal salt or a salt of an amino acid.

3. The method according to claim 2, wherein said salt is an amino acid salt of (R)-3-hydroxybutyric acid wherein the pH of the substitution fluid preparation is 5–8.

4. The method according to claim 2 or claim 3, wherein said amino acid is a natural neutral amino acid or a basic amino acid.

5. The method according to claim 1, wherein said (R)-3-hydroxybutyric acid is contained as a mixture of a (R)-isomer and a (S)-isomer.

6. The method according to claim 1, wherein said pharmaceutically acceptable carrier is at least one selected from the group consisting of sugars and inorganic salts.

* * * * *